US00PP32674P3

(12) United States Plant Patent
Post

(10) Patent No.: US PP32,674 P3
(45) Date of Patent: Dec. 22, 2020

(54) ***CHRYSANTHEMUM* PLANT NAMED 'DLFHED3'**

(50) Latin Name: ***Chrysanthemum* X *morifolium***
Varietal Denomination: DLFHED3

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 16/873,329

(22) Filed: Mar. 19, 2020

(65) Prior Publication Data

US 2020/0305323 P1 Sep. 24, 2020

Related U.S. Application Data

(60) Provisional application No. 62/919,611, filed on Mar. 20, 2019.

(51) Int. Cl.
*A01H 5/02* (2018.01)
*A01H 6/14* (2018.01)

(52) U.S. Cl.
USPC ..... Plt./286
CPC ..... *A01H 6/1424* (2018.05)

(58) Field of Classification Search
USPC ..... Plt./263.1, 284, 286
See application file for complete search history.

(56) References Cited

U.S. PATENT DOCUMENTS

PP14,950 P2 * 6/2004 Pieters ..... A01H 5/00 Plt./291

* cited by examiner

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Chrysanthemum* plant named 'DLFHED3', characterized by its upright plant habit; vigorous growth habit; freely branching habit; dark green-colored leaves; uniform and freely flowering habit; strong upright flowering stems with numerous inflorescences; spider-type inflorescences with yellow green-colored ray florets that become red purple in color with development giving a bi-colored appearance; and relative resistance to *Fusarium oxysporum* f. sp. *chrysanthemi* and *Puccinia horiana* strain PhNL1.

2 Drawing Sheets

Figure 1:
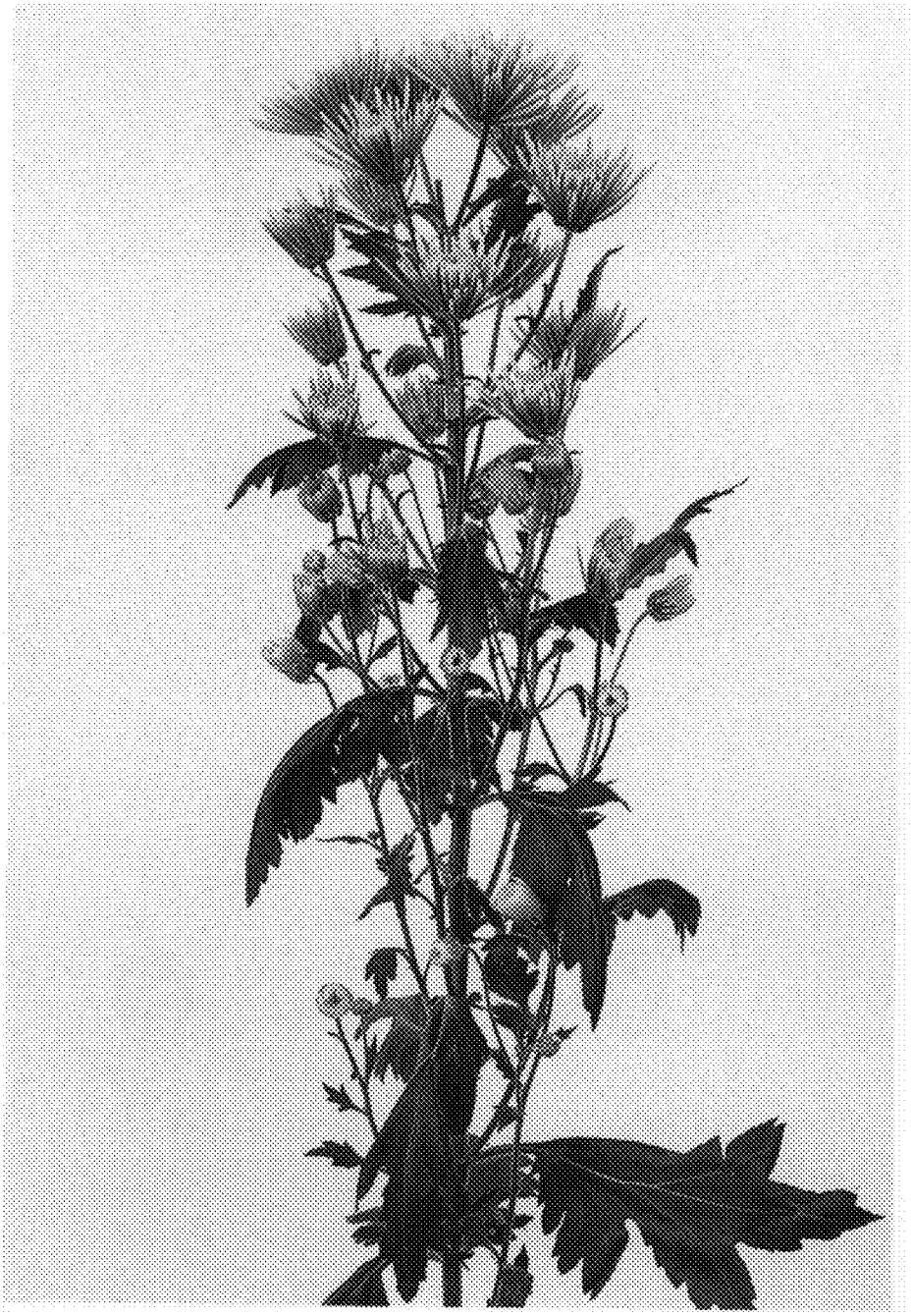

Botanical designation: *Chrysanthemum* X *morifolium*.
Cultivar denomination: 'DLFHED3'.

CROSS-REFERENCED TO CLOSELY-RELATED APPLICATIONS

Title: Varieties of *Chrysanthemum* Plants
Inventor/Applicant: Arie Gerard Post
Filed: Mar. 20, 2019
Ser. No. 62/919,611
Inventor/Applicant hereby claim the benefit of this provisional U.S. Patent Application.

STATEMENT REGARDING PRIOR DISCLOSURES BY INVENTOR/APPLICANT & ASSIGNEE

A Japanese Plant Breeder's Rights application for the instant plant was filed by the Assignee, Deliflor Royalties B. V. of Maasdijk, The Netherlands on Aug. 9, 2018, application number 33305. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFHED3'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in February, 2014 of a proprietary selection of *Chrysanthemum* x *morifolium* identified as code number DB 31733 as the female, or seed, parent with a proprietary selection of *Chrysanthemum* x *morifolium* identified as code number DB 38838 as the male, or pollen, parent. The new *Chrysanthemum* plant was discovered and selected as a single flowering plant from within the progeny of the stated cross-pollination in a controlled greenhouse environment in Maasdijk, The Netherlands in October, 2014.

Asexual reproduction of the new *Chrysanthemum* plant by vegetative terminal cuttings since October, 2014 in Maasdijk, The Netherlands, has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFHED3'. These characteristics in combination distinguish 'DLFHED3' as a new and distinct *Chrysanthemum* plant:

1. Upright plant habit; vigorous growth habit.
2. Freely branching habit.
3. Dark green-colored leaves.
4. Uniform and freely flowering habit.
5. Strong upright flowering stems with numerous inflorescences.
6. Spider-type inflorescences with yellow green-colored ray florets that become red purple in color with development giving a bi-colored appearance.
7. Relatively resistant to *Fusarium oxysporum* f. sp. *chrysanthemi* and *Puccinia horiana* strain PhNL1.

Plants of the new *Chrysanthemum* differ from plants of the female parent selection in ray floret color as ray florets of plants of the new *Chrysanthemum* are red purple and yellow green bi-colored whereas ray florets of plants of the female parent selection are yellow in color. In addition, inflorescences of plants of the new *Chrysanthemum* are not as dense as inflorescences of plants of the female parent selection.

Plants of the new *Chrysanthemum* differ from plants of the male parent selection in ray floret color as ray florets of plants of the new *Chrysanthemum* are red purple yellow green bi-colored whereas ray florets of plants of the male parent selection are white in color. In addition, ray florets of plants of the new *Chrysanthemum* are quilled in shape whereas ray florets of plants of the male parent selection are ligulate in shape.

Plants of the new *Chrysanthemum* can be compared to plants of *Chrysanthemum* X *morifolium* 'Anastasia Pink', disclosed in U.S. Plant Pat. No. 14,294. In side-by-side comparisons plants of the new *Chrysanthemum* differ primarily from plants of 'Anastasia Pink' in ray floret color as ray florets of plants of the new *Chrysanthemum* are darker in color than ray florets of plants of 'Anastasia Pink'. In addition, inflorescences of plants of the new *Chrysanthemum* are smaller than inflorescences of plants of 'Anastasia Pink'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1 of 2) comprises a side perspective view of a typical flowering stem of 'DLFHED3' grown as a spray-type cut flower.

Figure 2:
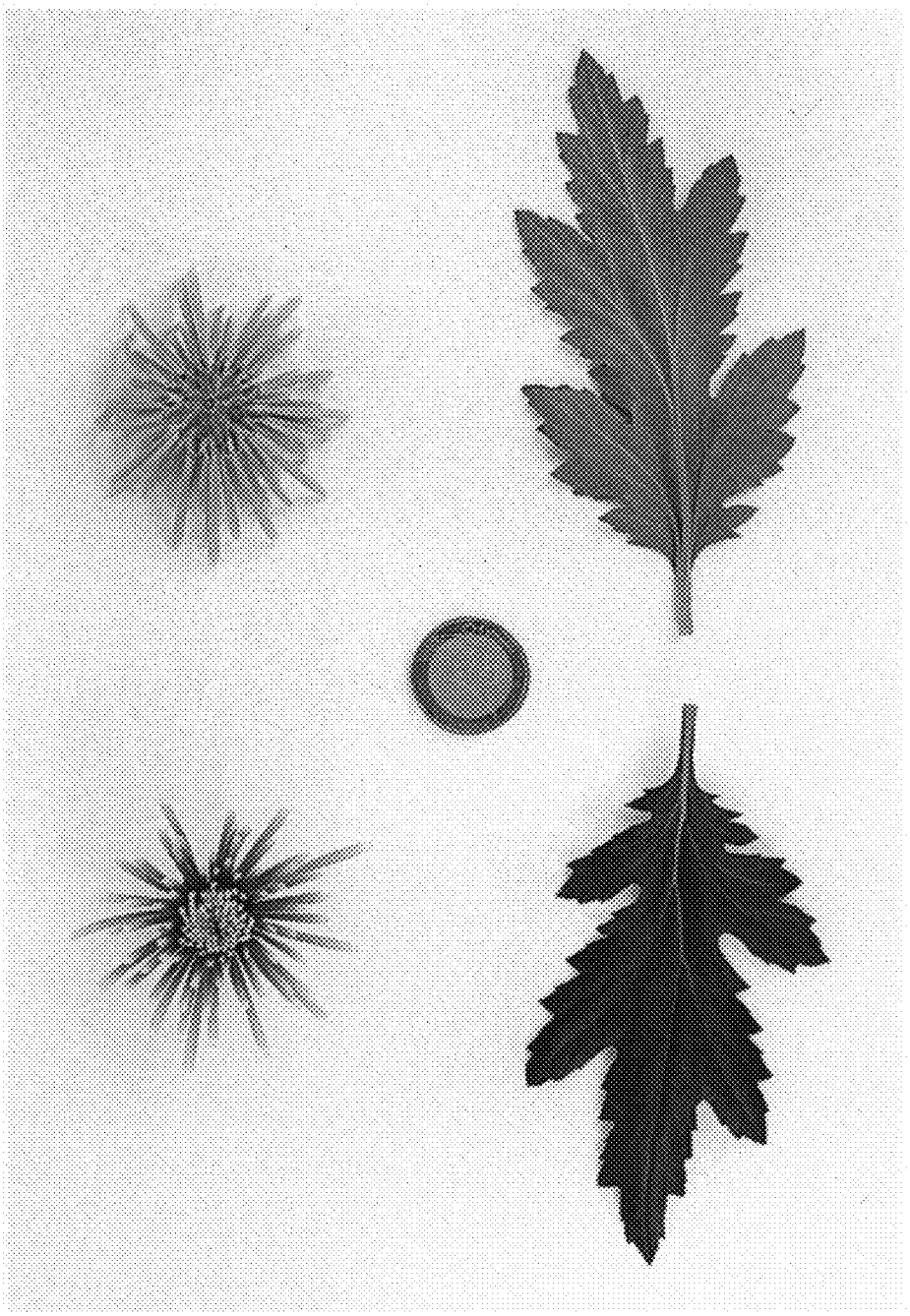

The photograph on the second sheen (FIG. 2 of 2) is a close-up view of lower (top of the photographic sheet) and upper (bottom of the photographic sheet) surfaces of typical inflorescences (left) and, leaves (right).

DETAILED BOTANICAL DESCRIPTION

The aforementioned photographs and following observations and measurements describe plants grown during the winter in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 2° C. to 20° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFHED3'.

Parentage:

*Female, or seed, parent*.—Proprietary selection of *Chrysanthemum* x *morifolium* identified as code number DB 31733, not patented.

*Male, or pollen, parent*.—Proprietary selection of *Chrysanthemum* x *morifolium* identified as code number DB 38838, not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous spider-type cut flower that is typically grown as a single stem spray-type; upright plant habit; vigorous growth habit and rapid growth rate.

*Plant height, soil level to top of foliar plane*.—About 76.3 cm.

*Plant height, soil level to top of inflorescence plane*.—About 80.1 cm.

*Plant (spray) diameter*.—About 15.6 cm.

*Flowering stem length*.—About 72.8 cm.

*Flowering stem diameter*.—About 6 mm.

*Flowering stem internode length*.—About 2.6 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 144A.

*Flowering stem color, developed*.—Close to 146B.

*Leaf description*.—Arrangement: Alternate; simple. Length: About 13.1 cm. Width: About 8.1 cm. Shape: Ovate to oblong. Apex: Short apiculate. Base: Attenuate. Margin: Palmately lobed, coarsely serrate; sinuses convergent and medium in depth. Texture and luster, upper surface: Moderately pubescent, not rugose; moderately velvety; very slightly glossy to matte. Texture and luster, lower surface: Moderately pubescent, prominent venation; slightly velvety; matte. Venation pattern: Pinnate, reticulate. Color: Developing leaves, upper surface: Close NN137A. Developing leaves, lower surface: Close to 147B. Fully developed leaves, upper surface: Close to between NN137A and 147A; venation, close to 147C. Fully developed leaves, lower surface: Close to 147B; venation, close to 146C. Petioles: Length: About 2.5 cm. Diameter: About 2.5 mm by 3 mm. Strength: Moderately strong. Texture and luster, upper and lower surfaces: Densely pubescent; slightly glossy. Color, upper surface: Close to 148A; edges, close to NN137A. Color, lower surface: Close to 146C. Stipules: Quantity and appearance: Two leafy stipules, opposite, at the petiole attachment to the stem. Length: About 9 mm. Width: About 9 mm. Shape: Flabellate. Texture and luster, upper surface: Moderately pubescent, not rugose; moderately velvety; very slightly glossy to matte. Texture and luster, lower surface: Moderately pubescent, prominent venation; matte. Color, upper surface: Close to between NN137A and 147A. Color, lower surface: Close to 147B.

Inflorescence description:

*Appearance*.—Spider-type inflorescence form with quilled-shaped ray florets and if present, tubular disc florets (disc florets are inconspicuous); inflorescences borne perpendicular to peduncles and face mostly upright to slightly outwardly; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 49 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 17 inflorescences develop per flowering stem.

*Inflorescence size*.—Diameter: About 7.2 cm. Depth (height): About 3.7 cm. Disc diameter: If present, about 1 mm to 2 mm.

*Receptacles*.—Height: About 3 mm. Diameter: About 5 mm. Shape: Flattened globular. Color: Close to 145A to 145B.

*Inflorescence buds*.—Height: About 1.5 cm. Diameter: About 1.5 cm. Shape: Roughly globular. Texture and luster: Distally, smooth and glabrous; proximally, slightly to moderately pubescent; slightly glossy. Color: Close to 137C; immature ray florets, close to N77B with apices, close to 150D.

*Ray florets*.—Quantity and arrangement: About 130 arranged in about five whorls. Length: About 3.5 cm; varying between 2.1 cm and 4.3 cm. Width: About 2 cm. Shape: Quilled. Apex: Praemorse. Base: Fused. Aspect: Initially upright to about 60° from vertical. Texture and luster, inner surface: Smooth, glabrous; slightly velvety; matte. Texture and luster, outer surface: Smooth, glabrous; slightly velvety; slightly glossy. Color: When opening, inner surface: Close to 75B; distally, close to 145C to 145D and proximally, close to 145B to 145C. When opening, outer surface: Close to 75A; distally, close to 145C to 145D and proximally, close to 145B to 145C. Fully opened, inner surface: Close to 75B and 75A; distally, close to between 145D to 150D and proximally, close to 145B; venation, similar to lamina colors; color does not change with development. Fully opened, inner surface: Close to NN74C to NN74D; distally, close to 150D and proximally, close to 145A to 145B; venation, similar to lamina colors; color does not change with development.

*Disc florets*.—Quantity and arrangement: If present, one to four massed at the center of the receptacle; disc florets inconspicuous. Length: About 8 mm. Diameter: About 1 mm. Shape: Lower 77.5% fused into a tube; upper 22.5% free. Apex: Narrowly acute. Margin, distally: Entire. Texture and luster, inner and outer surfaces: Smooth, glabrous; glossy. Color, when opening and fully opened, inner and outer surfaces: Distally, close to 154B and proximally, close to 145B to 145C.

*Involucral bracts*.—Quantity and arrangement: About 30 arranged in three whorls. Length: About 9 mm. Width: About 3 mm. Shape: Narrowly ovate. Apex: Obtuse. Base: Cuneate. Margin: Entire. Texture and luster, upper surface: Smooth, glabrous; glossy. Texture and luster, lower surface: Moderately pubescent; matte. Color, upper surface: Close to 143B; margins, translucent and close to 157A and 200B. Color, lower surface: Close to 137B; margins, translucent and close to 157A and 200B.

*Peduncles*.—Length, terminal peduncle: About 4.1 cm. Diameter, terminal peduncle: About 2 mm. Length, third peduncle: About 4.3 cm. Diameter, third peduncle: About 2 mm. Strength: Strong. Aspect, terminal peduncle: Mostly upright. Aspect, third peduncle: About 40° from the flowering stem axis. Texture and luster: Moderately pubescent; moderately glossy. Color: Close to 143A.

*Reproductive organs*.—Androecium: Present on disc florets only. Quantity: About five per floret. Filament length: About 3 mm. Filament color: Close to 150D. Anther size: About 0.5 mm by 3 mm. Anther shape: Narrowly oblong. Anther color: Close to 13A. Pollen amount: Scarce. Pollen color: Close to 14B. Gynoecium: Present on both ray and disc florets. Quantity:

One per floret. Pistil length: About 2 mm. Style length: About 1.75 mm. Style color: Close to 145C. Stigma diameter: About 1 mm. Stigma shape: Cleft, decurrent. Stigma color: Close to 153D. Ovary color: Close to 145D.

*Seeds and fruits*.—To date, seed and fruit production have not been observed on plants of the new *Chrysanthemum*.

Pathogen & pest resistance: Plants of the new *Chrysanthemum* have been observed to be relatively resistant to *Fusarium oxysporum* f. sp. *chrysanthemi*. To date, plants of the new *Chrysanthemum* have not been observed to be resistant to pests and other pathogens common to plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFHED3' as illustrated and described.

* * * * *